United States Patent [19]

Mueller

[11] Patent Number: 5,229,421

[45] Date of Patent: Jul. 20, 1993

[54] METHODS AND COMPOSITIONS FOR INHIBITING LIPOXYGENASE

[75] Inventor: Richard A. Mueller, Glencoe, Ill.

[73] Assignee: G. D. Searle & Co., Chicago, Ill.

[21] Appl. No.: 947,661

[22] Filed: Sep. 18, 1992

Related U.S. Application Data

[60] Division of Ser. No. 714,301, Jun. 12, 1991, which is a division of Ser. No. 360,963, Jun. 2, 1989, Pat. No. 5,047,593, which is a division of Ser. No. 196,927, May 20, 1988, Pat. No. 4,857,558, which is a continuation of Ser. No. 736,887, May 20, 1985, abandoned.

[51] Int. Cl.$^5$ .................... A61K 31/05; A61K 31/04; A01N 37/10
[52] U.S. Cl. .................... 514/545; 514/543; 514/886; 514/887; 560/17
[58] Field of Search .................. 560/17; 514/545, 543, 514/886, 887

[56] References Cited

U.S. PATENT DOCUMENTS

| | | | |
|---|---|---|---|
| 3,979,460 | 9/1976 | Hay | 260/609 |
| 4,029,812 | 6/1977 | Wagner et al. | 424/298 |
| 4,076,841 | 2/1978 | Wagner et al. | 424/324 |
| 4,078,084 | 3/1978 | Wagner et al. | 260/500 |
| 4,108,831 | 8/1978 | Cottman | 260/45.95 |
| 4,539,159 | 9/1985 | Johnson | 260/465 |
| 4,560,799 | 12/1992 | Spivack et al. | 568/47 |

FOREIGN PATENT DOCUMENTS

| | | | |
|---|---|---|---|
| 60799A1 | 2/1982 | European Pat. Off. | |
| 152022 | 8/1985 | European Pat. Off. | 568/47 |
| 2716125 | 4/1976 | Fed. Rep. of Germany | |
| 2509725 | 1/1983 | France | |
| 47-115575 | 6/1972 | Japan | |

| | | | |
|---|---|---|---|
| 1557622 | 12/1979 | United Kingdom | 213/24 |

OTHER PUBLICATIONS

Chem. Abs. 81, (21)135705b, p. 388, 1974, Fujisawa et al.
Chem Abs. 82, (18)112655s, p. 32, 1975, Fujisawa et al.
Chem. Abs. 82 (13)86191r, p. 506, 1975, Fujisawa et al.
Chem. Abs. 82, (13)86190q, 1975, Fujisawa et al.
Chem. Abs. 82, (13)86196w, 1973, Fujisawa et al.

*Primary Examiner*—Marianne M. Cintins
*Assistant Examiner*—Margaret J. Page
*Attorney, Agent, or Firm*—Mary Jo Kanady; Paul D. Matukaitis

[57] ABSTRACT

This invention encompasses compounds and pharmaceutical compositions comprising a pharmaceutical carrier and an effective lipoxygenase inhibiting amount of a compound of the formula:

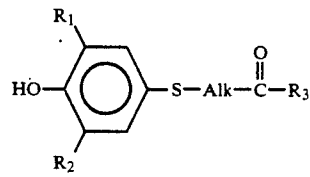

wherein $R_1$ and $R_2$ are the same or different members of the group consisting of 1,1-dimethylethyl, halo, phenyl and substituted phenyl wherein the substituents are selected from the group consisting of halo, hydroxy, lower alkyl and lower alkoxy, Alk is straight or branched chain lower alkylene; and $R_3$ is lower alkoxycarbonylloweralkyl.

15 Claims, No Drawings

METHODS AND COMPOSITIONS FOR INHIBITING LIPOXYGENASE

This is a division, of application Ser. No. 07/714,301 filed on Jun. 12, 1991, which is a divisional of application Ser. No. 07/360,963, filed on Jun. 2, 1989 now U.S. Pat. No. 5,047,593, which is a divisional of application Ser. No. 07/196,927 filed May 20, 1988 and issued as U.S. Pat. No. 4,857,558 on Aug. 15, 1989, which is a continuation of application Ser. No. 06/736,887, filed May 20, 1985 now abandoned.

BACKGROUND OF THE INVENTION

A. Field of the Invention

The present invention relates to compounds and pharmaceutical compositions which inhibit lipoxygenase and are useful as anti-inflammatory and anti-allergy agents.

It is well recognized that arachidonic acid, an unsaturated fatty acid, is the precursor of prostaglandins, thromboxanes, the 5-, 11-, 12- and 15-hydroxy eicosatetraenoic acids (HETEs, DIHETEs, TRIHETEs) and hydroperoxyeicosatetraenoic acids (HPETEs) and the leukotrienes all of which have profound physiological effects. The leukotrienes, which are produced via the 5-lipoxygenase pathway, are major contributors to the onset of the symptoms of asthma, and mediators for immediate hypersensitivity reactions and inflammation.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other immediate hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. The infiltration of eosinophils is one of the histologic features of a variety of allergic reactions.

With the exception of benoxaprofen, which has 5-lipoxygenase inhibition activity, aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid. These prostaglandin synthetase inhibitors generally exhibit anti-inflammatory, anti-pyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced pro-inflammatory effects. Administration of the NSAIDs alone can produce allergic reactions including bronchospastic reactivity; skin rashes; syndrome of abdominal pain, fever, chills, nausea and vomiting, and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs.

Prior to the recognition of the arachidonic acid cascade and the significance and interaction of the 5-lipoxygenase and other arachidonic acid cascade conversion products in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides secondary and tertiary alcohols which are inhibitors of the 5-lipoxygenase pathway and are useful in the treatment of asthma and other allergy and hypersensivity reactions, and many types of inflammation.

To date, benoxaprofen has been the only commercial anti-inflammatory agent which has 5-lipoxygenase inhibition activity. Prior to its withdrawal from the market because of untoward side effects, benoxaprofen was considered to represent a significant advance in the treatment of crippling arthritis and psoriasis. Thus, there remains a longstanding need for agents which block the mechanisms responsible for inflammation and allergic reactions, and which can be safely employed to treat, for example, arthritis, asthma, psoriasis and other dermatoses, allergic reactions and other 5-lipoxygenase mediated conditions. A need also exists for agents which can be administered with the inhibitors of other lipoxygenase enzymes, e.g. cyclo-oxygenase, to mitigate their side effects and support their desirable medicinal properties.

See Bengt Samuesson, "Leukotrienes: Mediators of Immediate Hypersensitivity Reactions and Inflammation", *Science*, Vol. 220, pp. 568-575 (May 1983); Michael K. Bach, "Inhibitors of Leukotriene Synthesis and Action", *The Leukotrienes, Chemistry and Biology*, pp 163-194 (Academic Press, Inc., 1984); C. W. Lee et al., "Human Biology and Immunoreactivity of Leukotrienes", *Advances in Inflammation Research*, Volume 6, pp 219-225 (Raven Press, New York 1984); Editorial, "Leukotrienes and other Lipoxygenase Products in the Patheognesis and Therapy of Psoriasis and Dermatoses", *Arch. Dermatol.*, Vol. 119, pp 541-547 (July 1983); Robert A. Lewis et al., "A Review of Recent Contributions on Biologically Active Products of Arachidonate Conversion", *Int. J. Immunopharmac.*, Vol. 4, No. 2, pp 85-90 (1982); Michael K. Bach, *Biochemical Pharmacology*, Vol. 23, No. 4, pp 515-521 (1984); and E. L. Becker, *Chemotactic Factors of Inflammation*, pp 223-225 (Eliver Science Publishers B.V., Amsterdam, 1983); Sharon, P. and Stenson, W. F., *Gastroenterology*, Vol. 84, 454 (1984); and Musch, M. W. et al., *Science*, Vol. 217, 1255 (1982).

The present invention provides compounds which block the 5-lipoxygenase pathway of the arachidonic acid cascade, block the formation of the leukotrienes therefore responsible for the allergy and inflammation, and hence and represent a new class of therapeutic agents which are useful in the treatment of allergic and hypersensitivity reactions and inflammation, alone, or in combination with cyclooxygenase inhibitors such as the non-steroidal anti-inflammatory agents.

B. Prior Art

Wagner et al. U.S. Pat. No. 4,029,812, and related U.S. Pat. Nos. 4,076,841 and 4,078,084 which issued from divisional applications of the -812 application, all assigned to the Dow Chemical Company, disclose 2-(3,5-di-tert-butyl-4-hydroxyphenyl)thiocarboxylic acids, esters and simple amides which are hypolipidemics and are useful in reducing plasma lipid levels, especially cholesterol and triglyceride levels. See also, German Offenlegenschrist DE 2716125 (1977).

The Wagner et al. and related compounds have also been reported in the literature as plasticizers and pesticides. See for Example Izv. vssh. uchenbn. zaved., Khim. Khim. Tekhnol. 20(4), 568–574 (1977); Pestic. Biochem. Physiol. 1979, 12(1), 23–30.

Primary sulfide alcohols having hindered phenol groups have been reported in the literature as plasticizers, stabilizers, anti-oxidants and elastomers. See U.S. Pat. No. 4,108,831; CA81(21:135705b; CA82(18):112655s; CA82(13):86191r; CA82(13):86190q; Eur. Pat. Appl. EP 60799 A1; and CA82(13):86196w.

Summary

This invention encompasses methods for inhibiting lipoxygenase and includes pharmaceutical formulations comprising a pharmaceutical carrier and an effective lipoxygenase inhibiting amount of a compound of the formula

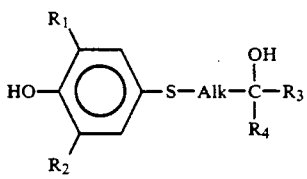

wherein: $R_1$ and $R_2$ are the same or different members of the group consisting of 1,1-dimethylethyl, halo, phenyl and substituted phenyl; Alk is straight or branched chain lower alkylene; $R_4$ is hydrogen or lower alkyl; $R_3$ is hydrogen or lower alkyl or a cycloalkyl group of from 3 to 8 carbon atoms.

The present invention also includes novel keto alcohols represented by Formula II:

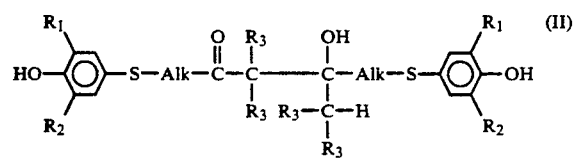

wherein $R_1$ and $R_2$ are the same or different members of the group consisting of 1,1-dimethylethyl, halo, phenyl or substituted phenyl; Alk is lower alkylene; $R_3$ is hydrogen or lower alkyl; with the limitation that $R_1$ each must be the same and $R_2$ each must be the same.

In addition, novel ketones/aldehydes represented by Formula III are provided by this invention.

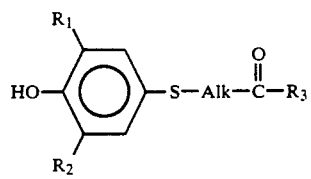

wherein $R_1$ and $R_2$ are the same or different members of the group consisting of 1,1-dimethylethyl, halo, phenyl and substituted phenyl, Alk is straight or branched chain lower alkylene; and $R_3$ is hydrogen, lower alkyl or lower alkoxycarbonylloweralkyl or cycloalkyl having 3 to 8 carbon atoms.

The compounds of Formula III are intermediates for the active compounds of Formula I and II. In addition, the compounds of Formula III are useful as anti-inflammatory anti-allergy agents and lipoxygenase inhibitors.

The phenylthioalcohols of this invention are most easily prepared by reaction of an appropriate ketone with an alkyl Grignard reagent or an alkyl lithium reagent. The alcohols can be obtained either by reduction of a ketone with, for example, sodium borohydride or by the addition of a Grignard or lithium reagent to the proper phenylthioaldehyde. The keto-alcohols are readily prepared by condensation of two equivalents of the appropriate ketone containing at least one hydrogen α to the carbonyl in the presence of a hindered or non-nucleophilic base. The phenylthioalkylketones are prepared by reaction of the desired thiol with a halo or tosyl ketone in the presence of a base. Alternatively, the thiol can be added to the double bond of an aliphatic unsaturated ketone. A third method of synthesis is by addition of an organometallic reagent, for example, an alkyl Grignard reagent, to an appropriate ester, acid chloride and the like. In addition, Alkylation of the lower alkoxycarbonyl lower alkyl substituted ketones leads to new lower alkoxy alkyl ketones which can then be hydrolyzed and decarboxylated in vivo or in vitro to the desired ketone.

It will be apparent to those skilled in the art that the compounds of this invention may be synthesized by other appropriate routes without departing from the spirit and scope of this invention.

The compounds of the present invention are useful in the treatment of allergy and hypersensitivity reactions and inflammation. The compounds are particularly useful in the treatment of arthritis and other inflammatory joint disease, asthma, proliferative skin disease such as psoriasis, and the like, alone or in combination with one or more cyclooxygenase inhibitors.

Detailed Description of Preferred Embodiments

The compounds of the present invention are generally administered in oral or parenteral dosages of from 0.1 to 100 mg/kg, preferably 0.5 to 50 mg/kg daily, preferably in divided dosages, to patients suffering from allergic or hypersensitivity reactions or inflammation, and are preferably applied topically to patients suffering from proliferative skin disease such as psoriasis. The compounds may be administered as the sole therapeutic agent, or in combination with other agents such as cyclooxygenase inhibitors, particularly in patients who exhibit pro-inflammatory or allergic response to, for example, conventional non-steroidal anti-inflammatory agents. Parenteral, e.g., intravenous, administration is preferable if a rapid response is desired, as, for example, in some cases of asthma.

The term "loweralkyl", as used herein, refers to straight or branched chain alkyl groups having from 1 to 6 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The term "lower alkylene", as used herein, refers to straight or branched chain alkylene groups having from 1 to 6 carbon atoms, i.e., methylene, ethylene, n-propylene, iso-propylene, n-butylene, sec-butylene, 1,1-dimethylethylene, n-pentylene, 2-methylbutylene, 2,2-dimethylpropylene, n-hexylene and the like.

The term "halo", as used herein, includes chloro, fluoro, bromo, and iodo.

The term "substituted phenyl" refers to phenyl having one or more substituents selected from the group consisting of halo, hydroxy, lower alkyl and lower alkoxy.

The term "lower alkoxy" refers to alkoxy groups having from 1 to 6 straight or branched chain carbon atoms, i.e., methoxy, ethoxy, n-propoxy, tert-butyloxy, etc.

The selective activity of the compounds of this invention was first determined using the following assays.

Test A-in vitro inhibition of soybean 15-lipoxygenase assay is employed to check the specificity of selected 5-lipoxygenase inhibitors. The oxygen-uptake during the oxidation of arachidonic acid to 15-HPETE by soybean lipoxygenase is measured in the presence and absence of inhibitors, using nordihydroguaiaretic acid (NDGA) as a reference standard. Compounds which inhibit at 100 $\mu$M are tested further to determine the $IC_{50}$ values. "IC" stands for "inhibitory concentration".

Test B- determination of anti-inflammatory, antiallergy activity: in vitro inhibition of 5-lipoxygenase. The 100,000 x g supernatant fraction of Rat Basophilic Leukemia Cell Homogenate (RBL-1) serves as a 5-lipoxygenase enzyme source. The enzyme is incubated with [1-$^{14}$C]-arachidonic acid and $CA^{++}$ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration.

Initial screening doses are 1 x $10^{-4}$M. When the compound inhibits more than 50% of 5-HETE synthesis at $10^{-4}$M, that compound is tested at multiple dose levels to determine the $IC_{50}$ value.

Test C- Inhibition of slow reacting substances (SRS) biosynthesis in cells. SRS synthesis by Rat Basophilic Leukemia Cell (REL-1) cells is induced by incubation of cells with ionophore A23187 alone and in combination with the test compound. The SRS released into the culture media is measured. The percent inhibition of SRS production is estimated by determining the doses of treated and control media needed in the tissue bath to produce equivalent contractions of segments of isolated guinea pig ileum. A compound that inhibits SRS biosynthesis by 50% or more is considered active at that concentration if an equivalent amount of the compound does not antagonize ileum contraction by SRS directly. If the compound directly inhibits the smooth muscle contractions, it will be considered inactive. Initial screening doses of test compounds are 1 x $10^{-4}$M and 1 x $10^{-5}$M.

Test-D- In vitro inhibition of human platelet 12-lipoxygenase. A 40,000 x g supernatant of platelet lysate is incubated with $^{14}$C-labeled arachidonic acid in the presence and absence of test compound. The conversion product, 12-hydroxyeicosatetraenoic acid (12-HETE), is quantitated after isolation by thin-layer chromatography. Compounds, initially screened at 100 $\mu$M concentration, which inhibit the synthesis of 12-HETE by 30% or more, are considered active. $IC_{50}$ values are determined for active compounds.

Test E- in vitro inhibition of sheep seminal vesicle microsome cyclooxygenase. Arachidonic acid cyclooxygenase reaction rates, in the presence or absence of test compounds, are determined by monitoring oxygen uptake. Compounds which inhibit at $10^{-4}$M are tested further to determine IC values.

The following examples further illustrate the present invention.

EXAMPLE 1

Preparation of
3,5-bis(1,1-dimethylethyl)-4-hydroxyphenyl thiocyanate

To a three-necked, round bottom 5 L flask, equipped with a mechanical stirrer, gas inlet, thermometer and gas outlet, was added 2,6-di-tert-butylphenol (474 g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1½ hours, maintaining the reaction mixture at a temperature of between 0° to 10° C. The reaction was stirred for an additional hour at 0° C., poured into 2 L of cold distilled water and refrigerated overnight. The aqueous phase was decanted and the solid taken up in methanol, precipitated from water, filtered and dried for 2 days over phosphorous pentoxide. The resulting gummy yellow solid was recrystallized from pentane and dried in vacuo to yield the product as a white powder, m.p. 61.5°-63° C. Analysis calc. for $C_{15}H_{21}NSO$:

Theory: C, 68.40; H, 8.03; N, 5.32; S, 12.17. Found: C, 68.85; H, 8.05; N, 5.29; S, 12.12

EXAMPLE 2

Preparation of
2,6-bis(1,1-dimethylethyl)-4-mercaptophenol 3,5-bis(1,1-Dimethylethyl)-4-hydroxyphenyl thiocyanate (55 g, 0.209 mole) was dissolved in acetone (200 ml) under an argon atmosphere. Water (7.2 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the structure of the product.

EXAMPLE 3

Preparation of 4-[[3,5-bis(1,1-dimethylethyl)-4-hydroxy phenyl]thio]2-butanone

The title compound of Example 2 (2.0 g) was dissolved in methanol (20 ml) and triethylamine (0.5 ml) added followed by methylvinylketone (0.0084 mole). The reaction was stirred under nitrogen for about 20 hours. 0.1N Hydrochloric acid (80 ml) was added and the aqueous phase extracted with ethyl ether. The organic extracts were dried over sodium sulfate, filtered, the solvent removed in vacuo and the residue chromatographed on silica to give the title compound, m.p. ca. 79°-81° C.

Analysis calc. for $C_{18}H_{28}O_2S(308.48)$: Calc.: C, 70.09; H, 9.15; S, 10.39. Found: C, 70.15; H, 9.00; S, 10.53.

EXAMPLE 4

3-[[3,5-bis(1,1-dimethylethyl)-4-hydroxyphenyl]thio]-propanal 2,6-bis(1,1-Dimethylethyl)-4-mercaptophenol (36.4 g, 0.15 mole) was dissolved in methanol (250 ml) in a 1 liter, round bottom, 3-necked flask equipped with a stirrer, gas inlet and gas outlet. The solution was flushed with argon and freshly distilled acrolein (25 g, 0.45 mole) and triethylamine (2.4 ml) were added dropwise over a one hour period and the solvent was evaporated on a rotary evaporator and the product purified by chromatography over silica, m.p. ca. 64°-65° C.

Analysis calc. for $C_{17}H_{26}O_2S(294.45)$ Calc.: C, 69.34; H, 8.90; S, 10.89. Found: C, 69.11; H, 8.79; S, 11.07.

EXAMPLE 5

Preparation of methyl 3-[[3,5-bis(1,1-dimethylethyl)-4-hydroxyphenyl]thio]-propanoate Following the procedure of Example 3, 2,6-(1,1-dimethylethyl)-4-mercaptophenol (5.00 g, 0.21 mole), methyl acrylate (5.40 g, 5.12 ml), triethylamine (0.5 ml) and methanol (50 ml) were combined and stirred under argon for 2 hours. The solvent and triethylamine was removed on a rotary evaporator and the residue concentrated to obtain 6.74 g of an oil. The product was purified by chromatography on silica and recrystallized from hexane to yield 2.87 g of the title product, m.p. ca. 63.5°-65.5° C.

Analysis calc. for $C_{18}H_{28}O_3S(392.6)$: Calc.: C, 66.62; H, 8.62; S, 9.88. Found: C, 66.93; H, 8.62; S, 9.87.

EXAMPLE 6

Preparation of Methyl 3-[[3,5-bis(1,1-dimethylethyl-4-hydroxyphenyl]sulfinyl]propanate The title compound of Example 5 (0.5 g, 0.0015 mole), meta-chloroper-benzoic acid (0.32 g, 0.0015 mole) and methylene chloride (25 ml) were stirred under argon for 12 hours. The excess peroxide was destroyed with a saturated potassium carbonate solution, the phases separated, washed with hexane and water, and dried over magnesium sulfate. The solid was filtered, recrystallized from ethyl ether and methylene chloride and dried in vacuo, m.p. ca. 106°-108° C.

Analysis calc. for $C_{18}H_{28}O_4S(340.48)$; Calc.: C, 63.50; H, 8.29; S, 9.42. Found: C, 63.60; H, 8.28; S, 9.45.

EXAMPLE 7

Preparation of ethyl 4-[[3,5-bis(1,1-dimethylethyl-4-hydroxyphenyl]thio]-3-oxobutanoate The title product of Example 2 (2,4 g, 0.01 mole) was dissolved in 8 ml of pyridine and 1.22 ml of ethyl 4-chloroacetoacetate was added dropwise by syringe. The reaction was stirred 1 hour under argon at room temperature. Ethyl ether (30 ml) and water (20 ml) were added, the layers separated and the organic phase extracted with 1N hydrochloric acid three times and water twice, then dried over sodium sulfate. After filtration, removal of solvent in vacuo and chromatograph on silica, the product (m.p. ca. 59°-63° C.) was obtained.

Analysis calc. for $C_{20}H_{30}O_4S$: Calc.: C, 65.53; H, 8.25; S, 8.74. Found: C, 65.72; H, 8.23; S, 8.67.

EXAMPLE 8

Preparation of 3-[[3,5-bis(1,1-dimethylethyl)-4-hydroxyphenyl]thio]-2-butanone

The title product of Example 2 (3.0 g, 0.0126 mole) was reacted with 3-chloro-2-butanone (1.27 ml) and triethylamine (1.7 ml) in ethyl ether (20 ml) at room temperature overnight. The mixture was filtered, the crystals washed with ethyl ether and the combined filtrates evaporated in vacuo. The crude product was chromatographed on silica then recrystallized from ethyl acetate/hexane to give the title compound m.p. ca. 94°-97° C.

Analysis calc. for $C_{19}H_{30}O_2S(308.48)$: Calc.: C, 70.08; H, 9.15; S, 10.39. Found: C, 70.28; H, 9.24; S, 10.61.

EXAMPLE 9

Preparation of 1-[[3,5-bis(1,1-dimethylethyl)-4-hydroxyphenyl]thio]-3-pentanone

The title compound of Example 2 (5.0 g, 0.021 mole) was reacted with ethylvinyl ketone (6.3 ml) and triethylamine (1 ml) in methanol (30 ml) by the method of Example 3 to give the title compound, m.p. ca. 76°-79° C.

Analysis calc. for $C_{19}H_{30}O_2S(322.50)$: Calc.: C, 70.76; H, 9.38; S, 9.94. Found: C, 71.03; H, 9.43; S, 9.70.

EXAMPLE 10

Preparation of 1-[[3,5-bis(1,1-dimethylethyl)-4-hydroxyphenyl]thio]-2-butanone

The thiol of Example 2 (7.1 g, 0.03M) was reacted with 1-bromo-2-butanone (5 g) and triethylamine (4.2 ml) in ethyl ether (25 ml) by the method of Example 8 to give the title compound, m.p. ca. 55°-57° C.

Analysis calc. for $C_{18}H_{28}O_2S(308.48)$: Calc.: C, 70.09; H, 9.15; S, 10.39. Found: C, 70.33; H, 8.93; S, 10.67.

EXAMPLE 11

Preparation of 5-[[3,5-bis(1,1-dimethylethyl)-4-hydroxyphenyl]thio]-2-pentanone

The thiol of Example 2 (5.0 g, 0.021M) was reacted with 5-chloro-2-pentanone (2.87 ml) and triethylamine (3.0 ml) in ethyl ether (50 ml) by the method of Example 8 to give the title compound, m.p. ca. 65°-67° C.

EXAMPLE 12

Preparation of 1-[[3,5-bis(1,1-dimethylethyl)-4-hydroxyphenyl]thio]-4-methyl-3-pentanone The thiol of Example 2 (4.76 g, 0.02 mole) was reacted with isopropylvinyl ketone (3.6 g) and triethylamine (3 ml) in methanol (50 ml) by the method of Example 3 to give the title compound, m.p. ca. 50°–53° C.

Analysis calc. for $C_{19}H_{30}O_2S(322.49)$: Calc.: C, 70.76; H, 9.38; S, 9.44. Found: C, 70.99; H, 9.18; S, 9.98.

EXAMPLE 12

Preparation of 1-[[3,5-bis(1,1-dimethylethyl)-4-hydroxyphenyl]thio]-4-methyl-3-pentanone The thiol of Example 2 (4.76 g, 0.02 mole) was reacted with isopropylvinyl ketone (3.6 g) and triethylamine (3 ml) in methanol (50 ml) by the method of Example 3 to give the title compound, m.p. ca. 50°–53° C.

Analysis calc. for $C_{20}H_{32}O_2S(336.52)$: Calc.: C, 71.39; H, 9.59; S, 9.52. Found: C, 71.57; H, 9.25; S, 9.66.

EXAMPLE 13

Preparation of 2,6-bis(1,1-dimethylethyl)-4-[(3-hydroxybutyl)thio]phenol

The title ketone of Example 3 (1.0 g, 0.0032 mole) was dissolved in 10 ml of absolute ethanol and the solution cooled to about 0° C. in an ice bath and 31 mg of sodium borohydride was added. The reaction wa stirred for about one hour and acetone was added. The solvents were removed in vacuo, the residue extracted twice with benzene, the organic extracts combined and dried over sodium sulfate. Removal of the solvent in vacuo gave the crude product which was chromatographed on silica to give the title compound.

Analysis calc. for $C_{18}H_{30}O_2S(310.5)$: Calc.: C, 69.63; H, 9.74; S, 10.33. Found: C, 69.43; H, 9.74; S, 10.28.

EXAMPLE 14

Preparation of 2,6-bis(1,1-dimethylethyl)-4-[(3-hydroxy-4-methylpentyl)thio]phenol 2.0 g of the aldehyde of Example 4 was dissolved in 20 ml of dry tetrahydrofuran under argon and added to 8.5 ml of 2M isopropylmagnesium chloride in tetrahydrofuran that had previously been added under argon gas to a flask that had been dried in vacuo overnight. Reaction temperature was maintained at 10°–15° C. with an ice bath. When addition was complete, the reaction mixture was allowed warm to room temperature and stirred for 3 hours. 2N hydrochloric acid (2 ml) was added followed by 50 ml of water and the mixture extracted with ethyl acetate three times. The organic extracts were combined, washed with water twice and dried over sodium sulfate. The solvent was removed in vacuo after filtration and the crude product chromatographed on silica to give the title compound.

Analysis calc. for $C_{20}H_{34}O_2S(338.54)$: Calc.: C, 70.96; H, 10.12; S, 9.47. Found: C, 71.29; H, 10.25; S, 9.43.

EXAMPLE 15

Preparation of 2,6-bis(1,1-dimethylethyl)-4-[(3-hydroxy-3,4-dimethylpentyl)thio]phenol 5 ml of 2.0M isopropylmagnesium bromide in tetrahydrofuran was cooled in an ice bath and a solution of the title compound of Example 3 (750 mg) in tetrahydrofuran (25 ml) was added dropwise under argon and the reaction mixture treated by the method of Example 14 to give the title compound.

Analysis calc. for $C_{21}H_{36}O_2S(352.52)$: Calc.: C, 71.54; H, 10.29; S, 9.09. Found: C, 71.44; H, 10.11; S, 9.36.

EXAMPLE 16

Preparation of α[2-[[3,5-bis(1,1-dimethylethyl)-4-hydroxyphenyl]thio]ethyl]cyclohexanemethanol By the method of Example 14, the aldehyde of Example 4 was reacted with 7.1 ml of 1.97M cyclohexyl magnesium bromide in tetrahydrofuran to give the title alcohol.

Analysis calc. for $C_{23}H_{38}O_2S(378.60)$: Calc.: C, 72.96; H, 10.42; S, 8.47. Found: C, 72.54; H, 10.61; S, 8.71.

EXAMPLE 17

Preparation of 2,6-bis(1,1-dimethylethyl)-4-[(3-hydroxy-3,4-dimethylpentyl)thio]phenol 40 ml of tetrahydrofuran was added to a flask that had been dried overnight at 100° C. in vacuo and 4.5 g (0.0134 mole) of the ketone of Example 12 was added. All processes were done under an argon atmosphere. The solution was cooled to about −50° C. in a dry ice/acetone bath and 19.16 ml (0.0268 mole) of 1.4M methyl lithium in tetrahydrofuran was added dropwise maintaining the temperature to about −60° C. to −50° C. When addition was complete, the reaction mixture was warmed to about 0° C. and 1N hydrochloric acid was added. The reaction mixture was extracted three times with ethyl acetate, the extracts combined, washed with water twice, dried over sodium sulfate, filtered and the solvent removed in vacuo. The residue was chromatographed on silica to give the title compound identical with that of Example 15.

EXAMPLE 18

Preparation of 2,6-bis(1,1-dimethylethyl)-4-[(3-ethyl-3-hydroxy-4-methylpentyl)thio]phenol 1.0 g (0.0032 mole) of the ketone of Example 10 was reacted with 4 ml of 2M isopropyl magnesium bromide in tetrahydrofuran by the method of Example 14 to give the title compound.

Analysis calc. for $C_{22}H_{38}O_2S(366.60)$: Calc: C, 72.08, H, 10.45; S, 8.75. Found: C, 71.68; H, 10.37; S, 9.08.

EXAMPLE 19

Preparation of 2,6-bis(1,1-dimethylethyl)-4-[(4-hydroxy-4,5-dimethylhexyl)thio]phenol The ketone of Example 11 (1.03 g, 0.0032 mole) was reacted with 0.008M (4 ml) of 2M isopropyl magnesium bromide by the method of Example 14 to give the title compound.

Analysis calc. for $C_{22}H_{38}O_2S(366.60)$:
Calc.: C, 72.08; H, 10.45; S, 8.75. Found: C, 72.06; H, 10.17; S, 8.66.

EXAMPLE 20

Preparation of 2,6-bis[[3,5-bis(1,1-dimethylethyl)-4-hydroxyphenyl]thio]-5-hydroxy-5-methyl-3-heptanone 25 ml (0.049 mole) of 2M isopropyl magnesium chloride was placed in a dried flask at room temperature under a nitrogen atmosphere and 6 g (0.0195 mole) of ketone from Example 8 in 25 ml of tetrahydrofuran was added dropwise with stirring. Stirring was continued for 28 hours. 2.2N hydrochloric acid was added and about 250 ml of water to pH about 2. The mixture was extracted with ethyl acetate (total of about 1 liter), extracts combined, dried over sodium sulfate, filtered and the solvent removed in vacuo. The crude product was chromatographed on silica to give the title compound, m.p. ca. 123°–128° C.

Analysis calc. for $C_{36}H_{56}O_4S_2$(616.96): Calc.: C, 70.08; H, 9.15; S, 10.39. Found: C, 70.38; H, 9.22; S, 10.42.

EXAMPLE 21

Preparation of 2,6-bis(1,1-dimethylethyl)-4-[(2-hydroxy1,2-dimethylpropyl)thio]phenol The ketone of Example 8 is reacted with methyl lithium by the method of Example 17 to give the title compound.

EXAMPLE 22

Preparation of 2,6-bis(1,1-dimethylethyl)-4-[(2R-hydroxy-2-methylbutyl)thio]phenol 1.0 g (0.0032M) of ketone from Example 10 was reacted with 0.0081M of methyl magnesium bromide by the method of Example 14 to give the title compound.

Analysis calc. for $C_{19}H_{32}O_2S$(324.51). Calc.: C, 70.32; H, 9.94; S, 9.88. Found: C, 70.26; H, 9.65; S, 9.99.

EXAMPLE 23

Preparation of 1,9-bis[[3,5-bis(1,1-dimethylethyl)-4-hydroxyphenyl]thio]-6-hydroxy-6-methyl-4-nonanone 1.03 g (0.0032M) of ketone from Example 11 was treated with 0.008M of isopropyl magnesium chloride (4 ml) in tetrahydrofuran by the method of Example 20 to give the title compound.

Analysis calc. for $C_{38}H_{60}O_4S_2$. Calc.: C, 70.76; H, 9.38; S, 9.94. Found: C, 70.70; H, 9.26; S, 9.67.

EXAMPLE 24

Preparation of 1-[[3,5-bis(1,1-dimethylethyl)-4-hydroxyphenyl]thio]-4-[[[3,5-bis(1,1-dimethylethyl)-4-hydroxyphenyl]thio]methyl]-4-hydroxy-3-methyl-2-hexanone 2M isopropyl magnesium bromide in tetrahydrofuran (4 ml, 0.008M) and 1.0 g of ketone (0.0032M) from Example 10 were reacted by the method of Example 20 to give the title compound.

Analysis calc. for $C_{36}H_{56}O_4S_2$(616.94). Calc.: C, 70.08; H, 9.14. Found: C, 69.78; H, 9.12.

EXAMPLE 25

Preparation of 1,7-bis[[3,5-bis(1,1-dimethylethyl)-4-hydroxyphenyl]thio]-5-hydroxy-5-methyl-3-heptanone 10.0 g (0.00324M) of ketone from Example 3 was reacted by the method of Example 20 with 40.5 ml (0.081M) of 2M isopropyl magnesium bromide in tetrahydrofuran to give the title product m.p. about 108°–110° C.

Analysis calc. for $C_{36}H_{56}O_4S_2$.

Calc.: C, 70.08; H, 9.15; S, 10.39. Found: C, 70.17; H, 9.18; S, 10.35.

EXAMPLE 26

Preparation of 2′-hydroxy [1,1′:3′,1″-terphenyl]-5′-yl thiocyanate 2,6,-Diphenylphenol (100.0 g, 0.406 mole) and ammonium thiocyanate (67.99 g, 0.893 mole) were suspended in methanol (150 ml) in a three-necked round bottom flask equipped with magnetic stirrer, thermometer and bubbler. The reaction mixture was cooled to −5° C. in an acetone/ice bath and chlorine gas bubbled through the solution for three hours. Maintaining the temperature below 10° C., ammonia gas was bubbled through the reaction for 2 hours. The contents of the flask were then poured into iced distilled water (250 ml) and allowed to stand for 12 hours in the refrigerator. After filtering, the solid was dried in vacuo at 45° C. for 12 hours. The title compound was purified by chromatography on silica and recrystallized from hexane, m.p. about 104°–106.5° C.

Analysis calc. for $C_{19}H_{13}OSN$ (303.39): Calc.: C, 75.22; H, 4.32; N, 4.62; S, 10.57. Found: C, 75.12; H, 4.49; N, 4.65; S, 10.41.

EXAMPLE 27

Preparation of 5′-mercapto[1,1′:3′,1″-terphenyl]-2′-ol

2′-hydroxy[1,1′:3′,1″-terphenyl]-5′-yl thiocyanate (32.2 g, 0.106 mole) was dissolved in acetone (150 ml) and water (1.9 ml), stirred and cooled to −5° C. Triethyl phosphine (15.7 ml, 0.106 mole) was added dropwise over a period of 40 minutes. The reaction was stirred at 0° C. for 1 hour and then at room temperature for 2 hours. The solvent was evaporated and the product isolated by chromatography on silica.

Analysis calc. for $C_{18}H_{14}OS$ (278.31). Calc.: C, 77.67; H, 5.07; S, 11.52. Found: C, 77.80; H, 5.19; S, 11.68.

EXAMPLE 28

Preparation of 3,5-dichloro-4-hydroxyphenyl thiocyanate 2,6-Dichlorophenol (100 g, 0.613 mole) and ammonium thiocyanate (102.73 g, 1.350 mole) were mixed in methanol and the solution cooled to 0° C. Chlorine gas was bubbled throught the reaction, maintaining the temperature below 10° C. The solution turned a pale yellow color. The reaction was stirred for a total of 3 hours until acidic, at which time ammonia gas was bubbled through and the solution stirred for an additional three hours at 0° to 10° C. The reaction was poured into iced distilled water, and filtered, yielding approximately 20 g of a yellow solid which was dried overnight in vacuo. The filtrate was extracted with ethyl acetate, the extracts dried over magnesium sulfate and solvent removed in vacuo to yield approximately 100 g of crude product. Following purification by silica chromatography, the material was taken up in 1 liter of toluene, charcoal added, filtered and recrystallized from hexane to yield 55.03 g of product as a yellow solid, m.p. about 94.5°–97° C. The structure was confirmed by NMR.

EXAMPLE 29

Preparation of 2,6-dichloro-4-mercaptophenol

Following the method of Example 2, the title compound was prepared from 3,5-dichloro-4-hydroxyphenyl thiocyanate. The structure was confirmed by NMR.

Analysis calc. for $C_6H_4OCl_2S(195.98)$. Calc.: C, 36.94; H, 2.07; Cl, 36.35; S, 16.44. Found: C, 36.96; H, 2.06; Cl, 36.31; S, 16.56.

EXAMPLE 30

By replacing 2,6-bis(1,1-dimethylethyl)-4-mercapto phenol with 2,6-dichloro-4-mercaptophenol in the above procedures, the following compounds are obtained:

3-[(3,5-dichloro-4-hydroxyphenyl)thio]propanal
methyl 3-[(3,5-dichloro-4-hydroxyphenyl)thio]propanoate
3-[(3,5-dichloro-4-hydroxyphenyl)thio]propanoic acid
2,6-dichloro-4-[(3-hydroxypropyl)thio]phenol
4-[(3,5-dichloro-4-hydroxyphenyl)thio]-2-butanone
ethyl 4-[(3,5-dichloro-4-hydroxyphenyl)thio]-3-oxobutanoate
3-[(3,5-dichloro-4-hydroxyphenyl)thio]-2-butanone
1-[(3,5-dichloro-4-hydroxyphenyl)thio]-3-pentanone
1-[(3,5-dichloro-4-hydroxyphenyl)thio]-2-butanone
5-[(3,5-dichloro-4-hydroxyphenyl)thio]-2-pentanone
1-[(3,5-dichloro-4-hydroxyphenyl)thio]-4-methyl-3-pentanone
1-[(3,5-dichloro-4-hydroxyphenyl)thio]-4-[[(3,5-dichloro-4-hydroxyphenyl)thio]methyl]-4-hydroxy-3-methyl-2-hexanone
1,9-bis[(3,5-dichloro-4-hydroxyphenyl)thio]-6-hydroxy-6-methyl-4-nonanone
2,6-bis[(3,5-dichloro-4-hydroxyphenyl)thio]-5-hydroxy-5-methyl-3-heptanone
2,6-dichloro-4-[(3-hydroxybutyl)thio]phenol
2,6-dichloro-4-[(3-hydroxy-4-methylpentyl)thio]phenol
2,6-dichloro-4-[(3-hydroxy-3,4-dimethylpentyl)thio]phenol
α-[2-[(3,5-dichloro-4-hydroxyphenyl)thio]ethyl]cyclohexanemethanol
1,7-bis[(3,5-dichloro-4-hydroxyphenyl)thio]-5-hydroxy-5-methyl-3-heptanone
2,6-dichloro-4-[(4-hydroxy-4,5-dimethylhexyl)thio]phenol
2,6-dichloro-4-[(3-ethyl-3-hydroxy-4-methylpentyl)thio]phenol

EXAMPLE 31

By replacing 2,6-bis(1,1-dimethylethyl)-4-mercapto phenol with 5'-mercapto[1,1':3',1"]-terphenyl]-2'-ol in the above procedures, the following compounds are obtained.

3-[(2'hydroxy[1,1':3'1"terphenyl[-5'-yl)thio]propanal
methyl 3-[(2'hydroxy[1,1':3'1"terphenyl]-5'-yl)thio]propanoate
3-[(2'hydroxy[1,1':3'1"terphenyl]-5'-yl)thio]propanoic acid
5'-[(3-hydroxypropyl)thio][1,1':3'1"-terphenyl]-2'-ol
4-[(2'hydroxy[1,1':3'1"terphenyl]-5'-yl-thio]-2-butanone
ethyl 4-[(2'hydroxy[1,1':3'1"terphenyl]-5'-yl)thio]-3-oxobutanoate
3-[(2'hydroxy[1,1':3'1"terphenyl]-5'-yl)thio]-2-butanone
1-[(2'hydroxy[1,1':3'1"terphenyl]-5'-yl)thio]-3-pentanone
1-[(2'hydroxy[1,1':3'1"terphenyl]-5'-yl)thio]-2-butanone
5-[(2'hydroxy[1,1':3'1"terphenyl]-5'-yl)thio]-2-pentanone
1-[(2'hydroxy[1,1':3'1"terphenyl]-5'-yl)thio]-4-methyl-3-pentanone
1-[(2'hydroxy[1,1':3'1"terphenyl]-5'-yl)thio]-4-[[(2'hydroxy[1,1':3'1"terphenyl]-5'-yl)thio]methyl]-4-hydroxy-3-methyl-2-hexanone
1,9-bis[(2'hydroxy[1,1':3'1"terphenyl]-5'-yl)thio]-6-hydroxy-6-methyl-4-nonanone
2,6-bis[(2'hydroxy[1,1':3'1"terphenyl]-5'-yl)thio]-5-hydroxy-5-methyl-3-heptanone
5'-[(3-hydroxybutyl)thio][1,1':3'1"-terphenyl]-2'-ol
5'-[(3-hydroxy-4-methylpentyl)thio][1,1':3'1"-terphenyl]-2'-ol
5'[(3-hydroxy-3,4-dimethylpentyl)thio][1,1':3'1"-terphenyl]-2'-ol
α-[2-[(2'hydroxy[1,1':3'1"terphenyl]-5'-yl)thio]ethyl]-cyclohexanemethanol
1,7-bis[(2'hydroxy[1,1':3'1"terphenyl]-5'-yl)thio]-5-hydroxy-5-methyl-3-heptanone
5'-[(4-hydroxy-4,5-dimethylhexyl)thio][1,1':3'1"-terphenyl]-2'-ol
5'-[(3-ethyl-3-hydroxy-4-methylpentyl)thio][1,1':3'1"-terphenyl]-2'-ol The active agents of this invention can be administered to animals, including humans, as pure compounds. However, it is advisable to first combine one or more of the active compounds with one or more suitable pharmaceutically acceptable carriers or diluents to attain a satisfactory size to dosage relationship and thereby obtain a pharmaceutical composition.

Pharmaceutical carriers which are liquid or solid can be employed. Solid carriers such as starch, sugars, talc and the like can be used to form powders which may be used for direct administration or to fill gelatin capsules. Suitable lubricants such as magnesium stearate, stearic acid, as well as binders and disintegrating agents may be included to form tablets. Additionally, flavoring and sweetening agents may be added.

Unit dosage forms such as tablets and capsules can contain any suitable, predetermined, therapeutically effective amount of one or more active agent and a pharmaceutically acceptable carrier or diluent. Generally speaking, solid oral unit dosage forms of the compound of this invention will contain from 1.75 to 750 mg per tablet of drug as the effective lipoxygenase inhibiting amount of the compound.

The compounds of this invention exhibit both oral and parenteral activity and accordingly can be formulated in dosage forms for either oral, topical, nasal or parenteral administration.

Solid oral dosage forms included capsules, tablets, pills, powders, granules and the like.

Liquid dosage forms for oral administration include emulsions, suspensions, solutions, syrups and the like containing diluents commonly used in the art such as water. Besides inert diluents, such preparations can also include adjuvants such as wetting agents, emulsifying and suspending agents, and sweetening, flavoring and perfuming agents.

Preparations for parenteral administration include sterile aqueous or non-aqueous solutions. Examples of nonaqueous solvents or vehicles are propylene glycol, polyethylene glycol, vegetable oils such as olive oil and injectable organic esters such as ethyl oleate. The parenteral preparations are sterilized by conventional methods.

The compounds of this invention may also be formulated for topical application, using carriers which are well known in the art, as well as intranasal aerosols.

The amount of active ingredient administered may be varied; however, it is necessary that the amount of active ingredient be such that a suitable dosage is given. The selected dosage depends upon the desired therapeutic effect, the route of administration and the duration of effect, and the duration of treatment. Generally speaking, oral dosages of from 0.1 to 100 mg/kg, preferable from 0.5 to 50 mg/kg of body weight daily are administered to patients in need of such treatment, preferably in divided dosages, e.g. three to four times daily. In the case of acute allergic or hypersensitivity reactions, it is generally preferable to administer the initial dosage via the parenteral route and continue parenteral administration until the patient is stabilized, and can be maintained, if necessary on oral dosing.

In the case of psoriasis and other skin conditions, it is preferred to apply a topical preparation of a compound of this invention to the affected area three or four times daily.

In treating asthma and arthritis with a compound of this invention, the compounds may be administered either on a chronic basis, or as symptoms appear. However, in the case of arthritis and other inflammatory conditions which can lead to deterioration of joints and malformations, it is generally preferable to administer the active agent on a chronic bsis.

When the compounds of this invention are co-administered with one or more cyclooxygenase inhibitors, they may conveniently be administered in a unit dosage form or may be administered separately. When the patient is allergic or hypersensitive to the cyclooxygenase inhibitor, it is preferred to initiate therapy with a compound of this invention prior to administration of the cyclooxygenase inhibitor.

A typical tablet of this invention can have the following composition:

| Ingredient | Mg/tablet |
|---|---|
| Active ingredient | 100 |
| Starch, U.S.P. | 57 |
| Lactose, U.S.P. | 73 |
| Talc, U.S.P. | 9 |
| Stearic acid | 12 |

It will be understood by those skilled in the art that the above examples are illustrative, not exhaustive, and that modifications may be made without departing from the spirit of the invention and the scope of the claims.

The invention claimed is:

1. A compound of the formula:

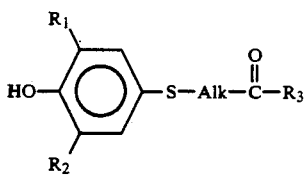

wherein $R_1$ and $R_2$ are the same or different members of the group consisting of 1,1-dimethylethyl, halo, phenyl and substituted phenyl wherein the substituents are selected from the group consisting of halo, hydroxy, lower alkyl and lower alkoxy, Alk is straight or branched chain lower alkylene; and $R_3$ is lower alkoxycarbonylloweralkyl.

2. A compound of claim 1 wherein $R_1$ and $R_2$ are each 1,1-dimethylethyl.

3. A compound of claim 1 wherein $R_1$ and $R_2$ are each halo.

4. A compound of claim 1 wherein $R_1$ and $R_2$ each are phenyl or substituted phenyl.

5. A compound according to claim 1 which is ethyl 4-[[3,5-bis(1,1-dimethylethyl)-4-hydroxyphenyl]thio]-3-oxobutanoate.

6. A pharmaceutical composition for use in the treatment of inflammatory or allergic conditions in mammals comprising a therapeutically effective amount of a compound of the formula

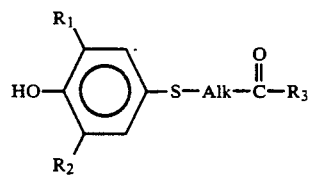

wherein $R_1$ and $R_2$ are the same or different members of the group consisting of 1,1-dimethylethyl, halo, phenyl and substituted phenyl wherein the substituents are selected from the group consisting of halo, hydroxy, lower alkyl and lower alkoxy, Alk is straight or branched chain lower alkylene; and $R_3$ is lower alkoxycarbonylloweralkyl and a pharmaceutically acceptable carrier.

7. A pharmaceutical composition according to claim 6 wherein said compound is ethyl 4-[[3,5-bis(1,1-dimethylethyl)-4-hydroxyphenyl]thio]-3-oxobutanoate.

8. A method of inhibiting lipoxygenase in a mammal which comprises administering to a mammal in need of such treatment an effective lipoxygenase inhibiting amount of a compound of the formula

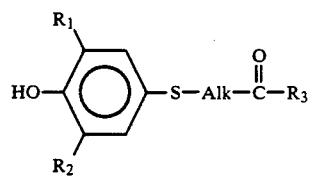

wherein $R_1$ and $R_2$ are the same or different members of the group consisting of 1,1-dimethlethyl, halo, phenyl and substituted phenyl, wherein the substituents are selected from the group consisting of halo, hydroxy, lower alkyl, and lower alkoxy; Alk is straight or branched chain lower alkylene; and $R_3$ is lower alkoxycarbonylloweralkyl.

9. A method according to claim 8 wherein $R_1$ and $R_2$ are each 1,1-dimethylethyl.

10. A method according to claim 8 wherein $R_1$ and $R_2$ are each halo.

11. A method according to claim 8 wherein $R_1$ and $R_2$ are each phenyl or substituted phenyl.

12. A method of treating an inflammatory or allergic condition in a mammal which comprises administering to a mammal in need of such treatment a therapeutically effective amount of a compound of the formula

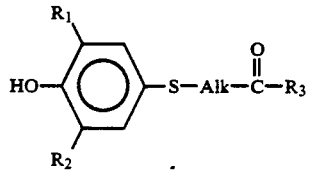

wherein $R_1$ and $R_2$ are the same or different members of the group consisting of 1,1-dimethylethyl, halo, phenyl and substituted phenyl, wherein the substituents are selected from the group consisting of halo, hydroxy, lower alkyl, and lower alkoxy; Alk is straight or branched chain lower alkylene; and $R_3$ is lower alkoxycarbonylloweralkyl.

13. A method according to claim 12 wherein $R_1$ and $R_2$ are each 1,1-dimethylethyl.

14. A method according to claim 13 wherein said compound is ethyl 4-[[3,5-bis(1,1-dimethylethyl)-4-hydroxyphenyl]thio]-3-oxobutanoate.

15. A method according to claim 12 wherein said condition is

* * * * *

UNITED STATES PATENT AND TRADEMARK OFFICE
CERTIFICATE OF CORRECTION

PATENT NO. : 5,229,421
DATED : July 20, 1993
INVENTOR(S) : Richard A. Mueller

It is certified that error appears in the above-indentified patent and that said Letters Patent is hereby corrected as shown below:

Column 9, line 45, reading "allowed warm" should read -- allowed to warm --.

Column 11, line 14, reading "[(2-hydroxyl,2-" should read -- [(2-hydroxy-1,2- --.

Column 12, line 46, reading "throught the" should read -- through the --.

Column 15, line 21, reading "a chronic bsis." should read -- a chronic basis. --.

Column 18, line 7, reading "condition is" should read -- condition is psoriasis. --.

Signed and Sealed this

Sixth Day of December, 1994

Attest:

BRUCE LEHMAN

Attesting Officer

Commissioner of Patents and Trademarks